US00PP09569P

United States Patent [19]

Glicenstein

[11] Patent Number: Plant 9,569

[45] Date of Patent: Jun. 4, 1996

[54] CHRYSANTHEMUM PLANT NAMED 'ZESTY BARBARA'

[75] Inventor: Leon Glicenstein, Salinas, Calif.

[73] Assignee: Yoder Brothers Inc., Barberton, Ohio

[21] Appl. No.: 366,475

[22] Filed: Dec. 30, 1994

[51] Int. Cl.[6] ..... A01H 5/00

[52] U.S. Cl. ..... Plt./76

[58] Field of Search ..... Plt./76, 81, 82

[56] References Cited

U.S. PATENT DOCUMENTS 4,616,099 10/1986 Sparkes ..... 47/58

OTHER PUBLICATIONS

Broertjes, et al., 1980, "A mutant of a mutant of a . . . Irradiation of progressive radiation–induced mutants in a mutation breeding programme with *Chrysanthemum morifolium*", Euphytica, 29:525–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods In the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X–rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in Chrysanthemum using X– and gamma radiation", Euphytica, 15:204–210.

*Primary Examiner*—Howard J. Locker
*Attorney, Agent, or Firm*—Foley & Lardner

[57] ABSTRACT

A Chrysanthemum plant named Zesty Barbara particularly characterized by its flat capitulum form; decorative capitulum type; red-purple ray floret color; diameter across face of capitulum of 32 to 41 mm when fully opened; branching pattern is spreading and prolific; natural season flower date of September 26 to 30 when planting rooted cuttings on June 15 to 18 in Hightstown, N.J.; plant height of 30 to 38 cm when grown in fall under natural daylength with no growth regulators in New Jersey; excellent, uniform growth habit; and good flexibility of plant for handling, packing and shipping.

1 Drawing Sheet

The present invention comprises a new and distinct cultivar of Chrysanthemum, botanically known as *Dendranthema grandiflora*, and referred to by the cultivar name Zesty Barbara.

Zesty Barbara, identified as 8516 (89-764A04), is a product of a mutation induction program. The new cultivar was discovered and selected by inventor Leon Glicenstein on Apr. 9, 1992 in a controlled environment in Salinas, Calif. as one flowering plant within a flowering block established as rooted cuttings from stock plants which had been exposed as unrooted cuttings to an X-ray source of 1500 rads in Fort Myers, Fla. on Oct. 24, 1991. The irradiated parent cultivar was the cultivar Barbara, disclosed in U.S. Plant Pat. No. 8,607, and described as a decorative garden mum with dark red-purple flower color.

The irradiation program resulting in Zesty Barbara has as its primary objective the expansion of color ranges of the parent cultivar Barbara. The irradiation program comprised irradiation cuttings of the parent cultivar at irradiation levels of 1500, 1750 and 2000 rads. A total of 618 cuttings harvested from a total of 225 irradiated plants were planted on Feb. 24, 10 and 3, 1992, respectively. Of these, 6 initial selections were made, which selections were then revegetated and reflowered. Three consecutive flowerings resulted in discarding 5 of the original 6 selections on Dec. 16, 1992. One code, which showed a mixture of colors, was reselected on Nov. 12, 1993, after which the original code was discarded. The remaining selection and reselection were maintained as PIs (Possible Introductions) and further trialed in Salinas, Calif., Hightstown, N.J. and Leamington, Ontario, Canada, ultimately resulting in the decision to introduce the one selection as Zesty Barbara, and the remaining selection as Fiery Barbara, disclosed in pending application Ser. No. 08/366,499.

The first act of asexual reproduction of Zesty Barbara was accomplished when vegetative cuttings were taken from the initial selection in June 1992 in a controlled environment in Salinas, Calif., by technicians working under supervision of Leon Glicenstein.

Horticultural examination of controlled flowerings of successive plantings has shown that the unique combination of characteristics as herein disclosed for Zesty Barbara are firmly fixed and are retained through successive generations of asexual reproduction.

Zesty Barbara has not been observed under all possible environmental conditions. The phenotype may vary significantly with variations in environment such as temperature, light intensity and daylength, without, however, any variance in genotype.

The following observations, measurements and comparisons describe plants grown in controlled open areas in Hightstown, N.J. Rooted cuttings were established in soil and maintained outdoors under the natural temperature and daylength prevailing during June through October.

The following traits have been repeatedly observed and are determined to be basic characteristics of Zesty Barbara, which, in combination, distinguish this Chrysanthemum as a new and distinct cultivar:

1. Flat capitulum form.
2. Decorative capitulum type.
3. Red-purple ray floret color.
4. Diameter across face of capitulum of 32 to 41 mm when fully opened.
5. Branching pattern is spreading and prolific.
6. Natural season flower date of September 26 to 30 when planting rooted cuttings June 15 to June 18 in Hightstown, N.J.

7. Plant height of 30 to 38 cm when grown in fall under natural daylength with no growth regulators in New Jersey.

8. Excellent, uniform growth habit.

9. Good flexibility of plant for handling, packing and shipping.

The accompanying photographic drawing is a color photograph of Zesty Barbara grown as a pinched garden mum under natural season outside conditions in Salinas, Calif., with the colors being as nearly true as possible with illustrations of this type. Plants were grown outside and dug and transplanted into 15 cm pots at flowering time for photography purposes.

Of the commercial cultivars known to the inventor, the most similar in comparison to Zesty Barbara is the parent cultivar Barbara. All traits of Zesty Barbara are similar to those of Barbara, except for the ray floret color and the number of disc florets. The ray floret color of Zesty Barbara is much more red in the red-purple group (R.H.S. 58A) than the red-purple color of Barbara (R.H.S. 72A). In addition, in most flowering trials, Zesty Barbara has more disc florets in the center of the flower than Barbara.

In the following description, color references are made to The Royal Horticultural Society Colour Chart. The color values were determined on plant material grown as a pinched garden mum grown under natural season outside conditions in Salinas, Calif. on Aug. 21, 1994.

Classification:

*Botanical.*—*Dendranthema grandiflora*, cv., Zesty Barbara.

*Commercial.*—Flat decorative garden mum.

INFLORESCENCE

Capitulum:

*Form.*—Flat.

*Type.*—Decorative.

*Diameter across face.*—32 to 41 mm when fully opened.

Corolla of ray florets:

*Color (general tonality from a distance of three meters).*—Red-purple.

*Color (upper surface).*—58A.

*Color (under surface).*24D, very strongly overlaid with 58A.

*Shape.*—Cross section concave, longitudinal section of outer ray florets straight.

Corolla of disc florets:

*Color (mature).*—9A.

*Color (immature).*—144C.

Reproductive organs:

*Androecium.*—Present on disc florets only; scant pollen.

*Gynoecium.*—Present on both ray and disc florets.

PLANT

General appearance:

*Height.*—30 to 38 cm when grown in fall under natural daylength with no growth regulators in New Jersey.

*Branching pattern.*—Spreading and prolific.

Foliage:

*Color (upper surface).*—147A.

*Color (under surface).*—147B.

*Shape.*—Small, slightly lobed, slightly serrated.

It is claimed:

1. A new and distinct Chrysanthemum plant named Zesty Barbara, as described and illustrated.

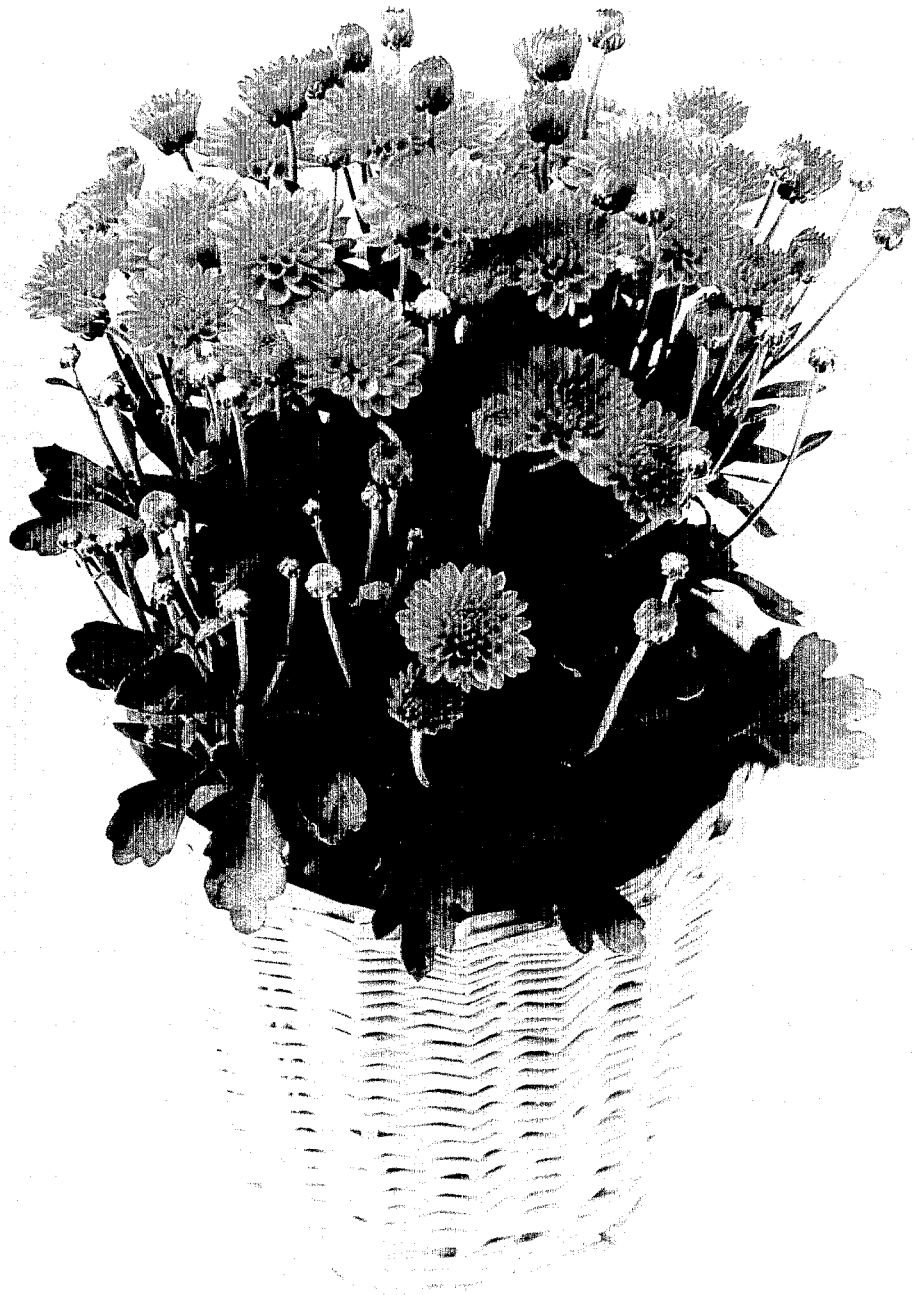

* * * * *